US006736815B2

(12) United States Patent
Ginn (10) Patent No.: US 6,736,815 B2
(45) Date of Patent: May 18, 2004

(54) APPARATUS AND METHODS FOR TREATING SPINAL DISCS (75) Inventor: Richard S. Ginn, San Jose, CA (US)

(73) Assignee: Core Medical, Inc., Sunnyvale, CA (US)

(*) Notice: Subject to any disclaimer, the term of this patent is extended or adjusted under 35 U.S.C. 154(b) by 203 days.

(21) Appl. No.: 09/947,785

(22) Filed: Sep. 6, 2001

(65) Prior Publication Data

US 2003/0045937 A1 Mar. 6, 2003

(51) Int. Cl.[7] ............................................... A61B 17/56
(52) U.S. Cl. ........................ 606/60; 606/61; 606/74
(58) Field of Search ............................... 606/60, 61, 86, 606/99, 74

(56) References Cited

U.S. PATENT DOCUMENTS

| 3,678,158 A | 7/1972 | Sussman |
| 3,875,595 A | 4/1975 | Froning |
| 3,941,127 A | 3/1976 | Froning |
| 3,944,114 A | 3/1976 | Coppens |
| 3,964,480 A | 6/1976 | Froning |
| 4,439,423 A | 3/1984 | Smith |
| 4,638,799 A | 1/1987 | Moore |
| 4,719,108 A | 1/1988 | Smith |
| 4,744,364 A | 5/1988 | Kensey |
| 4,772,287 A | 9/1988 | Ray et al. |
| 4,852,568 A | 8/1989 | Kensey |
| 4,863,477 A | 9/1989 | Monson |
| 4,878,915 A | 11/1989 | Brantigan |
| 4,904,260 A | 2/1990 | Ray et al. |
| 4,968,298 A | 11/1990 | Michelson |
| 5,015,247 A | 5/1991 | Michelson |
| 5,021,059 A | 6/1991 | Kensey et al. |
| 5,061,274 A | 10/1991 | Kensey |
| 5,114,032 A | 5/1992 | Laidlaw |
| 5,123,926 A | 6/1992 | Pisharodi |
| 5,192,301 A | 3/1993 | Kamiya et al. |
| 5,192,302 A | 3/1993 | Kensey et al. |
| 5,222,974 A | 6/1993 | Kensey et al. |
| 5,275,616 A | 1/1994 | Fowler |
| 5,306,254 A | 4/1994 | Nash et al. |

(List continued on next page.)

FOREIGN PATENT DOCUMENTS

WO    WO 01/28464 A1    4/2001

OTHER PUBLICATIONS

PCT Publication No. WO 97/26847, "Articulating Joint Repair," Felt et al., Jul. 31, 1987.
PCT Publication No. WO 99/02214, "Interbody Device and Method for Treatment of Osteoporotic Vertebral Collapse," Charles Ray et al., Jan. 21, 1999.
PCT Publication No. WO 00/69374, "Alloplastic Vertebral Disk Replacement," L. Easton et al. Nov. 23, 2000.
PCT Publication No. WO 00/71032 A2, "Hemostatic Device for Angioplasty," Marius Saines Nov. 30, 2000.

(List continued on next page.)

Primary Examiner—Eduardo C. Robert
(74) Attorney, Agent, or Firm—Orrick, Herrington & Sutcliffe LLP; James W. Geriak (57) ABSTRACT A band of biocompatible and/or bioabsorbable material is provided including threads on one or both of its ends. An area adjacent a spinal disc is accessed, and the band of material is wrapped around the disc to stabilize the disc and/or to facilitate healing. An elongate member is inserted around a posterior region of the disc, e.g., through tubular guide members. An end of the band is connected to a distal end of the elongate member, and the elongate member is pulled back around the disc to direct the band around the disc. The band is secured around the disc overlapping vertebrae adjacent the disc. Optionally, a relative location of the vertebrae is adjusted relative to the disc before wrapping the band around the disc, for example, using a fork member or traction. Energy may also be applied to the disc to enhance healing.

11 Claims, 6 Drawing Sheets

U.S. PATENT DOCUMENTS

| | | | |
|---|---|---|---|
| RE34,866 E | 2/1995 | Kensey et al. | |
| 5,411,520 A | 5/1995 | Nash et al. | |
| 5,549,679 A | 8/1996 | Kuslich | |
| 5,571,189 A | 11/1996 | Kuslich | |
| 5,601,556 A | 2/1997 | Pisharodi | |
| 5,645,565 A | 7/1997 | Rudd et al. | |
| 5,674,296 A | 10/1997 | Bryan et al. | |
| 5,690,674 A | 11/1997 | Diaz | |
| 5,720,748 A | 2/1998 | Kuslich et al. | |
| 5,728,146 A | 3/1998 | Burkett et al. | |
| 5,800,549 A | 9/1998 | Bao et al. | |
| 5,800,550 A | 9/1998 | Sertich | |
| 5,830,125 A | 11/1998 | Scribner et al. | |
| 5,865,846 A | 2/1999 | Bryan et al. | |
| 5,871,525 A | 2/1999 | Edwards et al. | |
| 5,888,220 A | 3/1999 | Felt et al. | |
| 5,888,223 A | 3/1999 | Bray, Jr. | |
| 5,888,224 A | 3/1999 | Beckers et al. | |
| 5,893,890 A | 4/1999 | Pisharodi | |
| 5,897,593 A | 4/1999 | Kohrs et al. | |
| 5,964,807 A | 10/1999 | Gan et al. | |
| 5,972,015 A | 10/1999 | Scribner et al. | |
| 5,972,031 A | 10/1999 | Biedermann et al. | |
| 6,001,130 A | 12/1999 | Bryan et al. | |
| 6,007,570 A | 12/1999 | Sharkey et al. | |
| 6,022,376 A | 2/2000 | Assell et al. | |
| 6,048,346 A | 4/2000 | Reiley et al. | |
| 6,056,749 A | 5/2000 | Kuslich | |
| 6,066,108 A | 5/2000 | Lundberg | |
| 6,066,154 A | 5/2000 | Reiley et al. | |
| 6,093,207 A | 7/2000 | Pisharodi | |
| 6,095,149 A | 8/2000 | Sharkey et al. | |
| 6,122,549 A | 9/2000 | Sharkey et al. | |
| 6,126,682 A | 10/2000 | Sharkey et al. | |
| 6,146,419 A | 11/2000 | Eaton | |
| 6,156,067 A | 12/2000 | Bryan et al. | |
| 6,183,518 B1 | 2/2001 | Ross et al. | |
| 6,206,921 B1 | 3/2001 | Guagliano et al. | |
| 6,206,922 B1 | 3/2001 | Zdeblick et al. | |
| 6,206,923 B1 | 3/2001 | Boyd et al. | |
| 6,221,109 B1 | 4/2001 | Geistlich et al. | |
| 6,248,131 B1 | 6/2001 | Felt et al. | |
| 6,482,235 B1 | 11/2002 | Lambrecht et al. | |
| 6,547,810 B1 | 4/2003 | Sharkey et al. | |
| 6,579,291 B1 * | 6/2003 | Keith et al. | 606/61 |
| 2002/0016583 A1 | 2/2002 | Cragg | |
| 2002/0077701 A1 | 6/2002 | Kuslich | |
| 2003/0181964 A1 * | 9/2003 | Sharkey et al. | 607/96 |

OTHER PUBLICATIONS

E.H. Cassinelli, M.D. et al., "Biochemistry of Intervertebral Disk Degeneration and the Potential for Gene Therapy Applications," SpineLine, The Clinical & News Magazine for Spine Care Professionals, vol. 11, Issue 1, Jan.–Feb. 2001.

Philip P. Finch, et al., PCT Publication No. WO 01/45579 Amendment, "Apparatus for Thermal Treatment of an Intervertebral Disc", Jun. 28, 2001.

Maurice Hiles, "New Specialty Polymer Products Through Interpenetrating Polymer Network (IPN) Technology—The Development of an Interpenetrating Polymer Network to Contain Mechanically Induced Vibration," Oct. 20–21, 1986, Colony Square Hotel, Atlanta, GA.

William F. McKay, PCT Publication No. WO 01/45577 A2, "Intervertebral Disc Treatment Devices and Methods", Jun. 28, 2001.

K. Nishimura, M.D., et al., "Percutaneous Reinsertion of the Nucleus Pulposus, An Experimental Study", SPINE vol. 23, No. 14, pp. 1531–1539, 1998.

W. Martin Belef, patent application Ser. No. 09/828,039 entitled "Methods for Treating Spinal Discs", filed on Apr. 6, 2001.

K. Nishimura, M.D. et al., "Percutaneous Reinsertion of the Nucleus Pulposus, An Experimental Study", SPINE vol. 23, No. 14, pp. 1531–1539, 1998.

* cited by examiner

APPARATUS AND METHODS FOR TREATING SPINAL DISCS

FIELD OF THE INVENTION

The present invention relates generally to treatment of spinal discs, and more particularly to apparatus and methods for treating ruptured or degenerated spinal discs using a band of material wrapped around the spinal disc.

BACKGROUND

Various apparatus and methods have been suggested for treating spinal discs when they rupture, degenerate, or otherwise become injured. For example, spinal fixation, i.e., fixing the vertebrae on either side of an injured disc relative to one another, is a commonly used treatment. This may involve inserting pedicle screws or other anchors into the vertebrae, and securing rods, wires, plates, and the like between the vertebrae, thereby substantially removing much of the forces acting on the disc during subsequent activity by the patient. In addition, the injured disc may be removed and a fixation system used to anchor the adjacent vertebrae, while the vertebrae are fused to one another. Such fixation and fusion procedures, however, may substantially impair free movement by the patient, because relative movement of the vertebrae is intentionally fixed.

In addition to fixation, an injured disc may be completely removed and replaced with a prosthesis. Alternatively, a portion of a disc may be removed, and a prosthesis used to fill the resulting cavity, such as those disclosed in U.S. Pat. Nos. 5,549,679 and 5,571,189, issued to Kuslich. In a further alternative, "hybrid" material may be implanted directly within a space created within a spinal disc, as disclosed in U.S. Pat. No. 5,964,807, issued to Gan et al., rather than removing the entire disc.

Accordingly, apparatus and methods for treating spinal discs would be considered useful.

SUMMARY OF THE INVENTION

The present invention is directed to apparatus and methods for treating spinal discs, and more particularly to apparatus and methods for treating a ruptured or degenerated spinal disc using a band of material wrapped around the spinal disc.

In accordance with one aspect of the present invention, an apparatus is provided for treating a ruptured or degenerated spinal disc that includes a band of material. The band of material, which may be formed from biocompatible and/or bioabsorbable material, may have a length sufficient to wrap around an exterior of a spinal disc, and may have a width sufficient to cover a spinal disc and at least partially cover at least one vertebra adjacent the spinal disc. In addition, one or both ends of the band may include a connector, e.g., threads, clips, and the like, for securing the ends to one another or to another portion of the band.

The band may include healing-promoting material coated thereon, impregnated therein or otherwise carried thereby. For example, an extra-cellular matrix material may be carried on at least one side of the band of material. Optionally, at least a portion of the band may be electrically conductive, and a source of electrical energy may be coupled to the electrically conductive portion of the band.

Optionally, the apparatus may include an elongate member that includes a proximal end including a handle thereon, and a curved distal end including a connector element thereon. The band may include a first end that is releasably connectable to the connector element on the elongate member. In an exemplary embodiment, the connector element includes a hook on the distal end of the elongate member, and one end of the band includes an opening for receiving the hook therein.

In addition, the apparatus may include a fork member including proximal and distal ends defining an axis therebetween. The distal end may include a pair of tines, each tine including a transverse portion extending generally parallel to one another transversely with respect to the axis. The transverse portion of each tine may include a tip and a heel disposed proximal to the tip. A length between the tip and the heel may be sufficient for engaging a first vertebra with the tip and pivotally engaging a second vertebra with the heel to adjust a d stance between the first and second vertebrae.

In another embodiment, the apparatus may include a guide member including a proximal end and a curved distal end having a radius of curvature corresponding substantially to an exterior perimeter of a spinal disc. The guide member generally includes a lumen extending between the proximal and distal ends, the lumen having a size for receiving the band of material therethrough. Preferably, the lumen through the guide member is a slot including a height greater than a width of the band, the slot preferably having a height that extends substantially perpendicularly to the radius of curvature of the distal end. More preferably, the apparatus includes a pair of such guide members that are opposite hand from one another.

In accordance with another aspect of the present invention, a method is provided for treating a ruptured or degenerated spinal disc of a patient. Initially, an area adjacent an exterior of a spinal disc disposed between adjacent vertebrae is accessed. A band of material, such as that described above, may be wrapped around the disc to stabilize the disc in a desired position relative to surrounding anatomy. Preferably, the band engages at least one of the vertebrae when the band is wrapped around the disc to substantially secure the disc relative to the at least one of the vertebrae.

In one embodiment, this may involve extending a distal end of an elongate member along a first lateral region of the disc around a posterior region of the disc to an opposite second lateral region of the disc. A first end of the band may be connected to the distal end of the elongate member, and the elongate member may be pulled back around the posterior region of the disc, thereby directing the first end of the band around the posterior region of the disc. At least one of the first end and a second end of the band may be secured to another portion of the band, thereby securing the band around the disc.

In another embodiment, a tubular guide member may be inserted around a portion of the exterior of the disc, and the band may be inserted through the guide member to facilitate wrapping the band around a posterior region of the disc. Preferably, a pair of opposite-hand tubular guide members may be inserted around opposing lateral regions of the exterior of the disc. The band may be inserted directly through the guide members or may be directed through the guide members using an elongate member previously advanced through the guide members, which may be used to pull the band through the guide members.

Optionally, a location of at least one of the vertebrae may be adjusted relative to the disc before wrapping the band around the disc. For example, at least one of the vertebrae may be engaged between tines of a fork member, and the tines may be manipulated between the vertebrae to increase a space between the vertebrae. Alternatively, the patient may be subjected to traction.

If desired, an extra-cellular matrix material may be placed between the band and the disc, e.g., to promote healing of the disc. For example, one or more layers of extra-cellular matrix material may be carried on an interior surface of the band such that the extra-cellular matrix material is placed against the disc when the band is wrapped around the disc.

In addition, energy may be applied to the disc to enhance healing of the disc. For example, at least a portion of the band may be electrically conductive, and a source of electrical energy may be coupled to the electrically conductive portion of the band. Electrical energy may be applied to the disc via the electrically conductive portion of the band, or alternatively, energy may be applied directly to the disc, e.g., using a separate energy device.

In accordance with yet another aspect of the present invention, a method is provided for treating a spinal region of a patient. An area adjacent an anterior region of a spinal disc may be accessed, for example, by creating an incision in a ligament surrounding the disc to access an exterior of the disc. An instrument may be inserted between the ligament and the exterior of the disc, e.g., through the incision, in order to access a posterior region of the disc. A diagnostic or therapeutic procedure may be performed that involves accessing the posterior region of the disc.

For example, a tubular guide member may be inserted around a portion of the exterior of the disc, e.g., between the ligament and the disc until a distal end of the instrument is disposed adjacent the posterior region of the disc. One or more instruments may then be introduced through the tubular guide member to access the posterior region. For example, an imaging device, such as an endoscope, may be inserted through the guide member or directly between the ligament and the disc to the posterior region. The imaging device may be used to observe the posterior region and/or to otherwise assist in diagnosing a patient's condition.

In addition to or instead of imaging, a therapeutic procedure may be performed at the posterior region of the disc. For example, a discectomy or other procedure may be performed that involves removing at least a portion of the disc from the posterior region, e.g., nucleus pulposus material that has leaked from within the disc. A therapeutic agent may be introduced into the posterior region or surrounding tissue to promote healing, pain relief, and the like. In addition, a band may be wrapped around the disc to stabilize the disc in a desired position relative to surrounding anatomy, as described above. In addition, tissue structures adjacent the posterior region of the disc, such as a facet joint or spinal cord, may be accessed from the posterior region to perform an intervention involving the accessed structure. Thus, the apparatus and methods of the present invention may provide a minimally invasive approach for accessing the posterior region of a spinal disc, while minimizing exposure of the disc and/or the spinal column adjacent the disc.

Other objects and features of the present invention will become apparent from consideration of the following description taken in conjunction with the accompanying drawings.

DETAILED DESCRIPTION OF THE PREFERRED EMBODIMENTS

Figure 1:
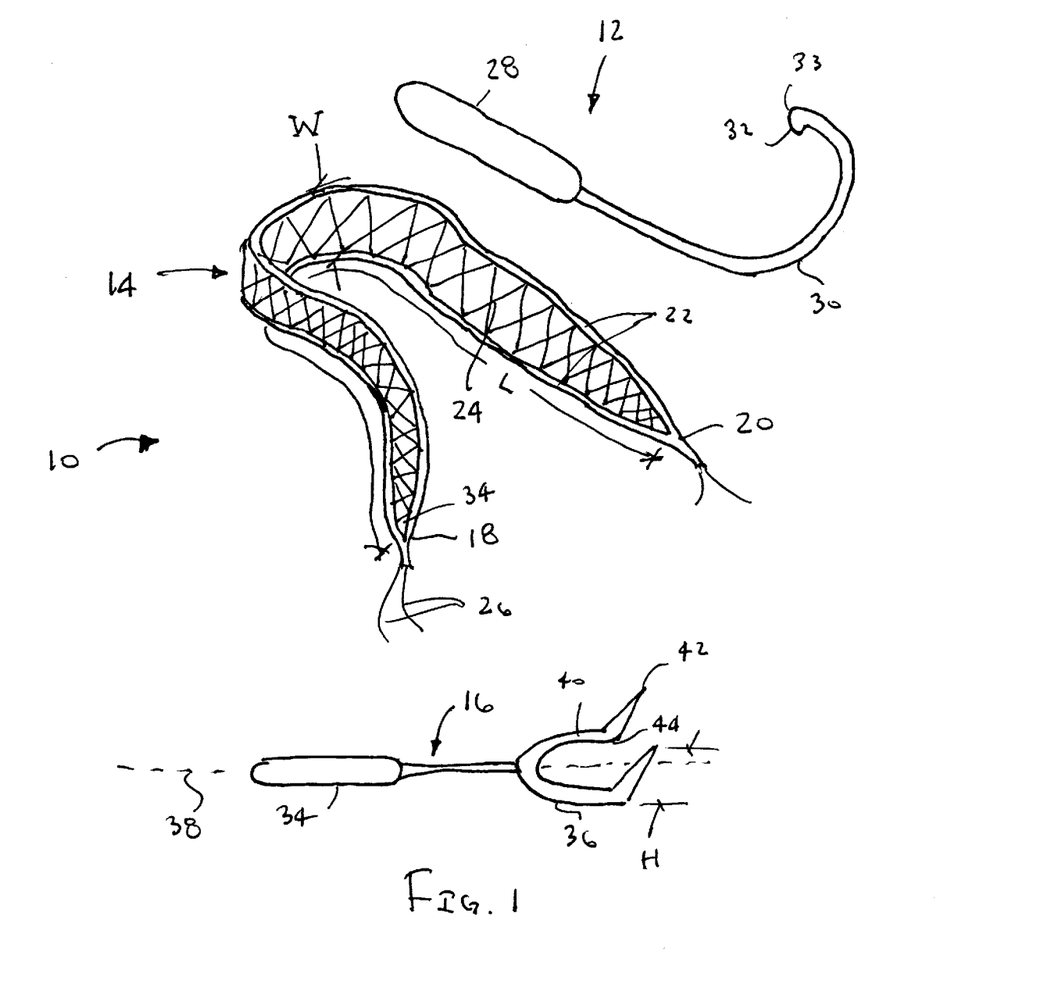
FIG. 1 is a perspective view of a first embodiment of a system for treating spinal discs, in accordance with the present invention.

Turning now to the drawings, FIG. 1 shows a first embodiment of an apparatus 10 for treating a spinal disc (not shown), in accordance with the present invention. The apparatus 10 generally includes a grasper 12, and a band of material 14 releasably connected to the grasper 12. Optionally, the apparatus 10 may also include a fork member 16, as shown, for adjusting adjacent vertebrae (not shown).

The band of material 14 is an elongate panel of biocompatible material having first and second ends 18, 20 defining a length "L" therebetween and defining a width "W." Preferably, the length "L" is sufficiently long such that the band 14 may be wrapped around an exterior perimeter of a spinal disc (not shown) and the ends 18, 20 overlapped or otherwise secured with one another. The width "W" may be sufficiently wide to cover an entire surface of a spinal disc, and preferably is sufficiently wide to cover a spinal disc and at least partially cover one or both vertebrae on either side of the spinal disc (not shown).

The band 14 may include one or more panels of substantially nonporous material, or alternatively, of porous material. In the exemplary embodiment shown, the band 14 includes a pair of spaced apart strips or filaments 22 that extend between the first and second ends 18, 20. Webbing 24, e.g., made from one or more fibers, extend between the strips 22. The strips 22 and/or webbing may be formed from inelastic materials, or alternatively may be formed from elastic materials, which may enhance stabilization of a spinal disc about which the band 14 is wrapped, as explained further below.

In a preferred embodiment, at least a portion of the band 14, and preferably all of the band 14, is bioabsorbable, such that it may remain within a patient's body until absorbed through natural excretion. In addition, the band 14 may include one or more healing-promoting materials within the band 14 and/or otherwise carried by the band 14. For example, an antibiotic, a steroid, an nsaid, an autologous therapeutics agent, e.g., a concentrated growth factor, or other therapeutic compounds, may be impregnated within or coated over the strips 22 and/or webbing 24. Alternatively, or in addition, the band 14 may carry one or more layers of naturally occurring extra-cellular matrix material, such as intestinal submucosa, stomach submucosa, bladder submucosa, and the like, e.g., along one or both side surfaces of the band 14.

At least one of the first and second ends 18, 20 of the band 14 may include a connector (not shown) for securing the ends 18, 20 to another portion of the band 14. For example, the first and second ends 18, 20 may be secured to one another for securing the band 14 around a spinal disc. Preferably, threads 26 extend from one or both ends 18, 20 for tying the ends 18, 20 to one another or to another portion of the band 14. Alternatively, one or more clips (not shown) may be attached (or attachable) to one of the ends 18, 20 that may be engaged with the band 14 on or adjacent the other of the ends 18, 20. In a further alternative, sutures or other threads (not shown) may be stitched between the first and second ends 18, 20 and/or elsewhere through the band 14 to secure the band 14 around a spinal disc.

In an alternative embodiment, at least a portion of the band 14 may be electrically conductive. For example, the strips 22 and/or the webbing 24 may include insulated electrically conductive pathways, e.g., wires, and/or electrically exposed areas, e.g., defining electrodes (not shown). A source of electrical energy, such a radio frequency ("RF") generator (also not shown), may be coupled to the conductive pathways, e.g., by coupling the energy source to one or both ends 18, 20 of the band 14. Alternatively, a separate device (not shown) may be provided that may be coupled to a source of energy, such as an RF generator, a laser, and the like, for applying energy directly to one or more regions of a spinal disc. The device may include a handle on one end and an electrode, lens, or other element on its other end for applying energy.

Returning to FIG. 1, the grasper 12 is an elongate member including a proximal end 28 having a handle, and a curved distal end 30 having a hook or other connector element 32 thereon. The distal end 30 preferably terminates in a rounded distal tip 33 to facilitate substantially atraumatic insertion of the distal end 30 between tissue structures. The hook 32 may be configured for releasably connecting one of the ends 18, 20 of the band 14 to the distal end 30 of the grasper 12. For example, the first end 18 of the band 14 may include a hole, slot, pocket, or other aperture 34 for receiving the hook 28 therein. The grasper 12 may be formed from a substantially rigid biocompatible material, such as stainless steel, or may be semi-rigid such that the distal end 26 may be bent or otherwise formed based upon a specific anatomical situation, as explained further below. In a further alternative, the distal end 26 may be a flexible or semi-rigid wire that is biased to a predetermined curvature corresponding to an exterior perimeter of a spinal disc, but may be resiliently deflectable to other configurations, e.g., a substantially straight configuration, to facilitate insertion of the grasper 12 into a surgical site.

The fork member 16 includes proximal and distal ends 34, 36 defining an axis 38 therebetween. The distal end 36 includes a pair of tines 40 that include transverse portions that extend generally parallel to one another substantially transversely with respect to the axis 38. The tines 40 may extend away from one another in a curved configuration that defines a space therebetween corresponding to a portion of a spinal disc. Preferably, each of the tines 40 terminates in a distal tip 42 and includes a heel 44 disposed proximal to the tip 42, e.g., at a base of the transverse portion of the respective tine 40. A height "H" between the tips 42 and the heels 44 may be sufficiently long to facilitate engaging and/or manipulating adjacent vertebrae, as described further below.

Turning to FIGS. 2A–2D, 3A, and 3B, the apparatus 10 may be used to treat a spinal disc 90 that has ruptured, become misaligned, and/or otherwise degenerated. Generally, the disc 90 is disposed between first and second vertebrae 92, 94 with a spinal cord 96 disposed adjacent the vertebrae 92, 94. For simplification, only the body portions of the vertebrae 92, 94 are shown, and other surrounding tissue structures, including the spinous process and transverse process of the vertebrae, nerve bundles extending from the spinal cord, and the like, have been eliminated.

Initially, the disc 90 may be accessed using conventional surgical procedures. Preferably, a surgical field is opened adjacent an exterior perimeter of the disc 90 that is exposed from an anterior approach, i.e., from a chest side of the patient. An anterior approach may be particularly useful for accessing and treating discs between the cervical vertebrae, because of the minimal amount of intervening tissue between the skin and the spinal column. An anterior approach may also avoid having to work around the spinous process and transverse process portions of the vertebrae in order to gain access to the spinal disc 90.

Figure 2A:
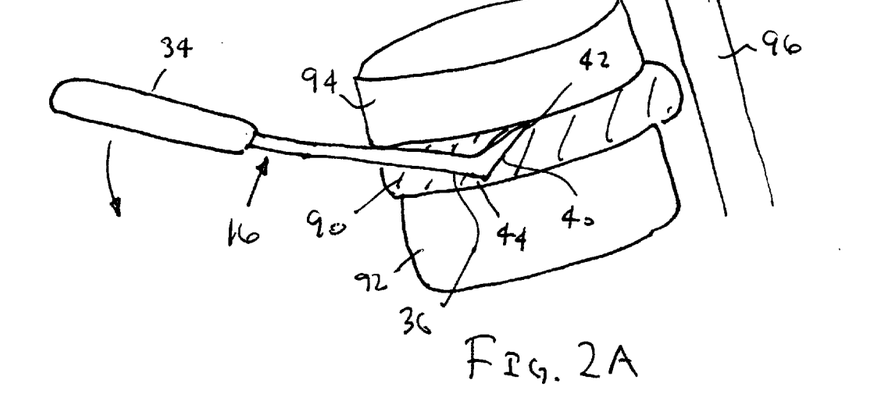
FIGS. 2A–2D are perspective views of a portion of an exposed spinal column, showing a method for treating a spinal disc using the apparatus of FIG. 1.
Figure 2B:
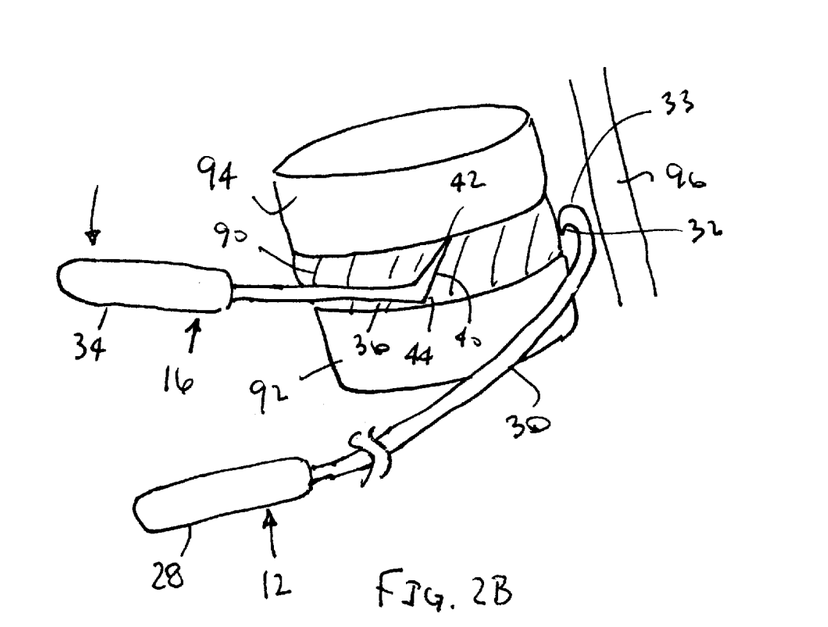

A location of at least one of the vertebrae 92, 94 may be adjusted relative to the disc 90 and/or relative to the other of the vertebrae 92, 94, e.g., to allow adjustment of the disc 90 if it has slipped or otherwise become misaligned. For example, as shown in FIG. 2A, the fork member 16 may be inserted around the disc 90, such that the tines 38 straddle the disc 90. The fork member 16 may be adjusted until the heels 42 engage the first vertebra 92 and the tips 40 engage the second vertebra 94. The fork member 16 may then be pivoted with the heels 42 against the first vertebra 92 such that the tips 40 move the second vertebra 94 away from the first vertebra 92 to increase a space between the vertebrae 92, 94, as shown in FIG. 2B.

The fork member 16 may then be stabilized, for example, manually or by securing the proximal end 34 to a support, e.g., fixed to a surgical table (not shown). Alternatively, the patient may be subjected to traction in order to increase the spacing between and/or otherwise realign the vertebrae 92, 94, as is well known in the art. If desired, the disc 90 may be adjusted, aligned, or otherwise manipulated, e.g., to prevent the disc 90 from impinging upon the spinal cord 96 or other nerves (not shown), and/or to create a channel around the perimeter of the disc 90. In addition, any nucleus pulposus (not shown) that has leaked through fissures in the annulus fibrosis of the disc 90 may be removed.

Returning to FIG. 2B, the distal end 30 of the grasper 12 may then be inserted around one lateral region of the disc 90 towards the posterior region of the disc 90, i.e., between the disc 90 and the spinal cord 96. Because of the rounded distal tip 33, the distal end 30 may be advanced around the disc 90 substantially atraumatically until the distal tip 33 becomes accessible around the opposite lateral region of the disc 90.

Figure 2C:
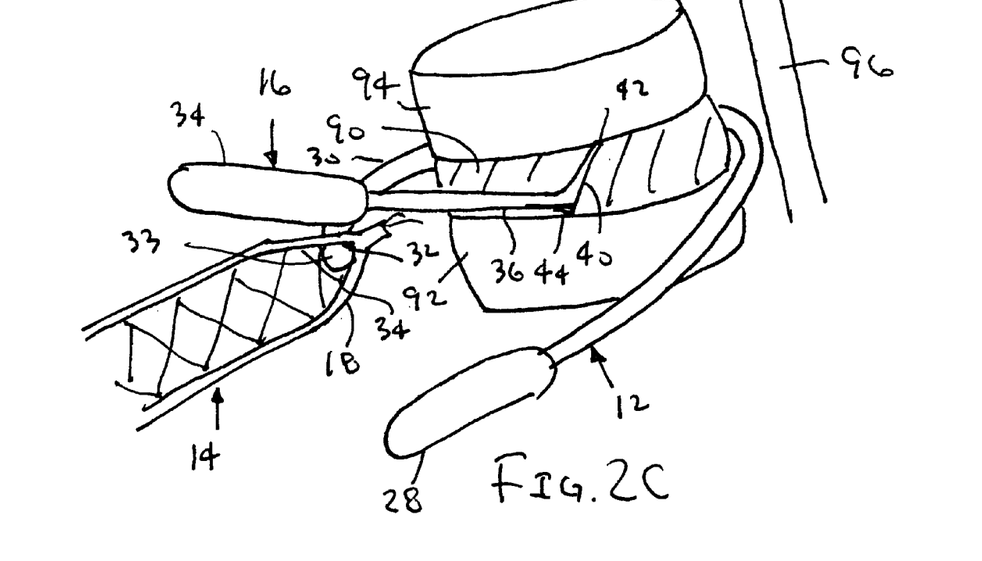
Figure 2D:
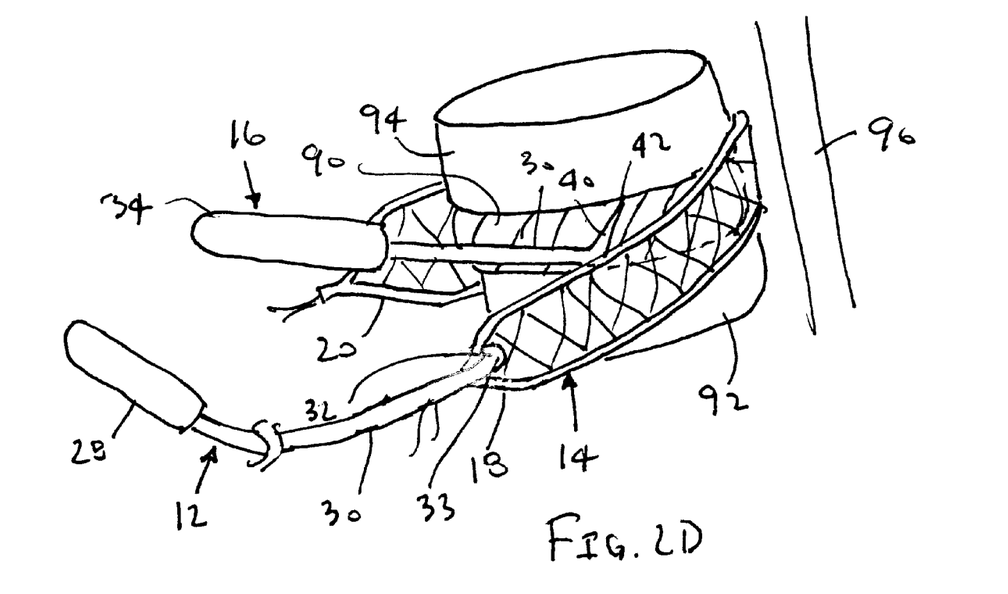

As shown in FIG. 2C, with the distal end 30 of the grasper 12 accessible, the first end 18 of the band 14 may be connected to the distal end 30, for example, by receiving the hook 32 through the hole 34 in the band 14. The grasper 12 may then be pulled back around the disc 90, thereby directing the first end 18 of the band 14 around the posterior region of the disc 90, as shown in FIG. 2D.

Figure 3A:
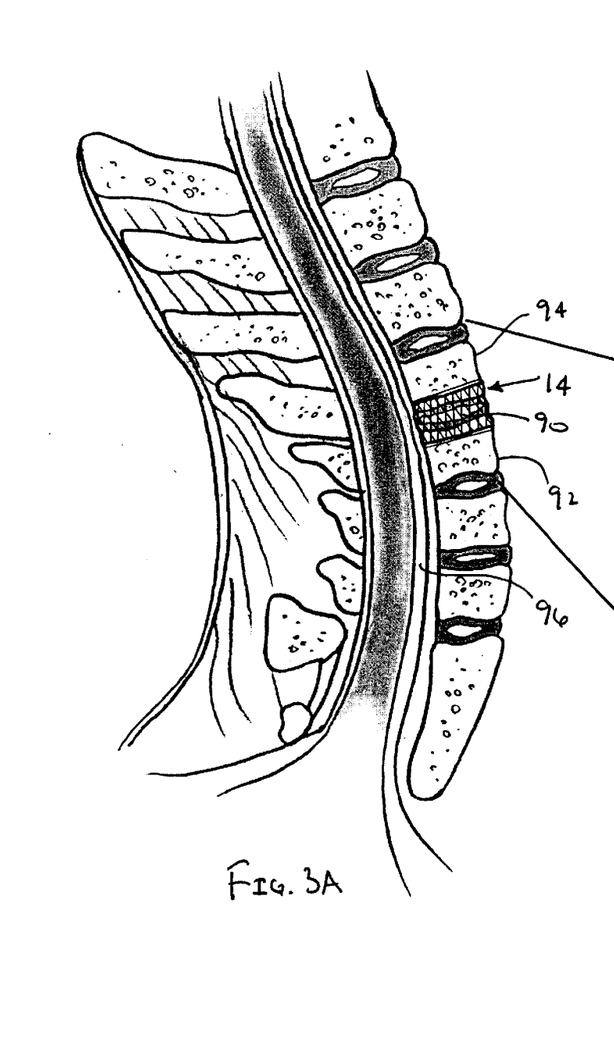
FIGS. 3A and 3B are side views of a spinal column, showing a band of material implanted to treat a spinal disc, in accordance with the present invention.
Figure 3B:
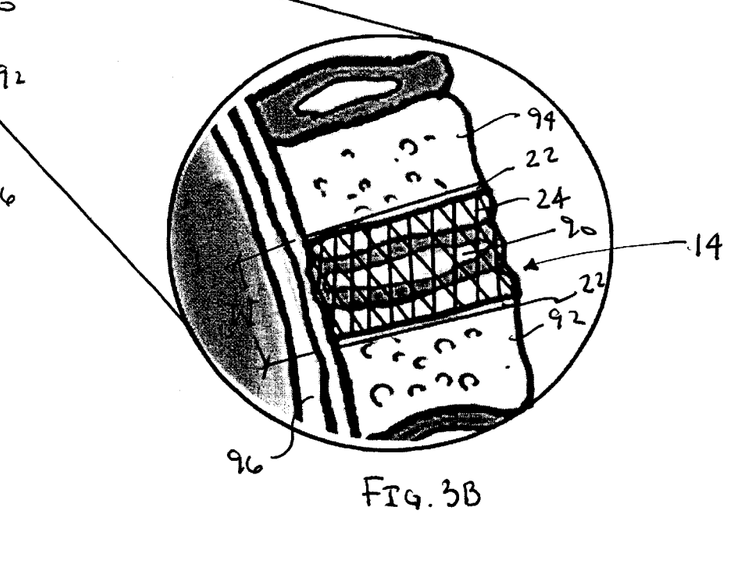

Once the band 14 has been directed around the posterior region of the disc 90, the fork member 16 may be removed, and the band 14 secured tightly around the disc 90, as shown in FIGS. 3A and 3B. To accomplish this, the first end 18 of the band 14 may be released from the grasper 12, and the first and second ends 18, 20 of the band 14 may be secured to one another. For example, threads 26 (not shown, see FIG. 1) on the first and second ends 18, 20 may be tied to one another. In this embodiment, the first and second ends 18, 20 may not overlap one another, but may end in close proximity to one another such that the threads 26 may be tied together. Alternatively, one of the first and second ends 18, 20 may be lapped over the other, and the threads 26 on the overlying end tied to an underlying portion of the band 14. In a further alternative, one or more clips, sutures, or other mechanical fasteners (not shown) may be used to secure the ends 18, 20 to one another or to another portion of the band 14. In yet another alternative, an adhesive may be used to secure the ends 18, 20, and/or mere frictional contact between the overlying end and the underlying portion may adequately secure the band 14 around the disc 90.

Preferably, the band 14 is subjected to sufficient tension when it is wrapped around the disc 90 to stabilize the disc 90 and/or to secure the disc 90 relative to one or both adjacent vertebrae 92, 94. To enhance this tension, all or a portion of the band 14 may be formed from elastic material, such that the band 14 may be stretched tightly around the exterior perimeter of the disc 90. If the band 14 is formed from elastic material, it may also allow the fork member 16 to be removed after the band 14 has been secured around the disc 90.

The band 14 may be sufficiently wide to cover the width of the disc. 90 Preferably, the band 14 has a width "W" that is wider than the disc 90 such that the band 14 overlaps one or both adjacent vertebrae 92, 94, as shown in FIG. 3B. Thus, when the band 14 is tightened, the disc 90 may also be secured in substantial alignment with the adjacent vertebrae 92, 94.

In the embodiment shown, the band 14 includes an open webbing 24, and consequently is porous. Thus, the band 14 may merely provide structural support for the underlying disc 90, e.g., to stabilize the disc 90 relative to the adjacent vertebrae 92, 94. In addition, the band 14 may compress the disc 90, consequently squeezing closed any fissures, holes, and the like that have occurred in the annulus fibrosis of the disc 90. Alternatively, the band 14 may be formed from a substantially nonporous panel of material such that the band 14 may substantially seal any fissures in the disc 90, thereby preventing nucleus pulposus material, and the like from leaking through the annulus fibrosis.

In yet a further alternative, a substantially nonporous material (not shown) may be provided between the band 14 and the exterior of the disc 90. For example, one or more layers of naturally occurring extra-cellular material, may be carried on an interior surface of the band 14 such that the material may be placed between the band 14 and the disc 90. In addition to sealing any fissures, such material may also promote healing, as is well known to those skilled in the art. Alternatively, or in addition, other materials that promote healing may be coated on and/or impregnated within the band 14.

If the band 14 is formed from bioabsorbable material, the band 14 may remain around the disc 90 until it is absorbed by the patient's body. Alternatively, the band 14 may be merely biocompatible such that the band 14 may remain within the patient's body indefinitely or until the disc 90 has sufficiently healed. In the latter example, a follow-up procedure may be performed to release the ends 18, 20 of the band 14 and pull the band 14 around the disc 90 to remove it from the patient's body.

In another embodiment, energy may be applied to the disc 90 to enhance healing, to cause scarring, and/or to enhance sealing of fissures or other leaks in the disc 90. For example, as described above, at least a portion of the band 14 may be electrically conductive. A source of electrical energy, e.g., an RF generator (not shown), may be coupled to the electrically conductive portion of the band 14. Once the band 14 is secured around the disc 90, electrical energy may be applied to the disc via the electrically conductive portion of the band 14. The power of the electrical energy may be relatively low, e.g., merely to enhance healing of the disc 90. Alternatively, the power may be relatively high, thereby causing scarring of the annulus fibrosis of the disc 90, which may seal fissures through which nucleus pulposus may leak.

Figure 4A:
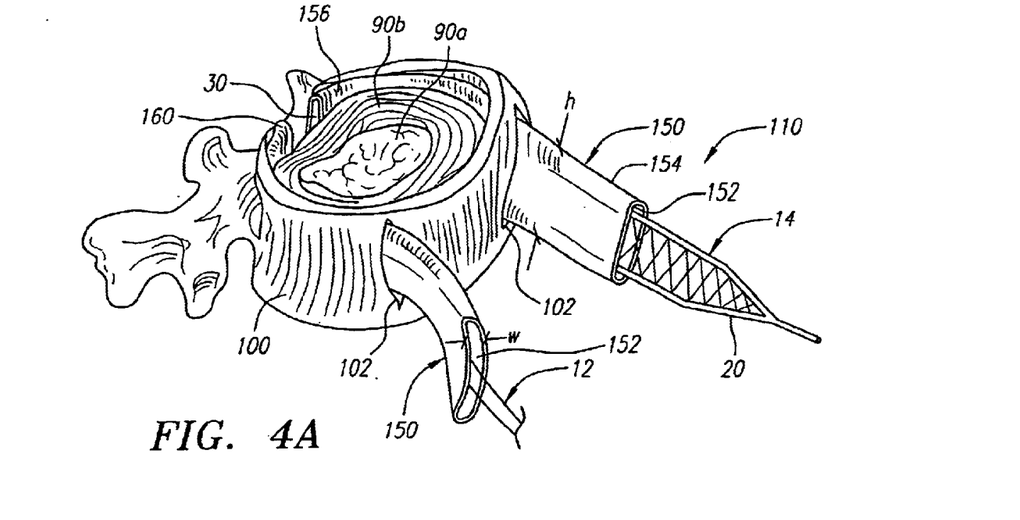
FIGS. 4A and 4B are perspective views of a spinal disc, showing a method for treating the spinal disc using another embodiment of an apparatus, in accordance with the present invention.
Figure 4B:
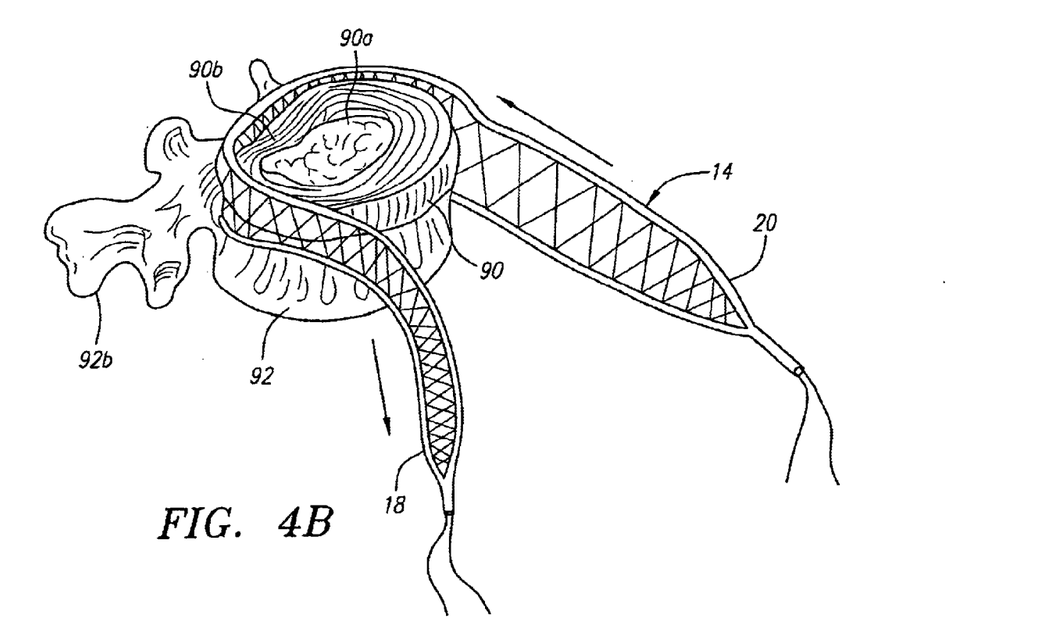
Figure 5:
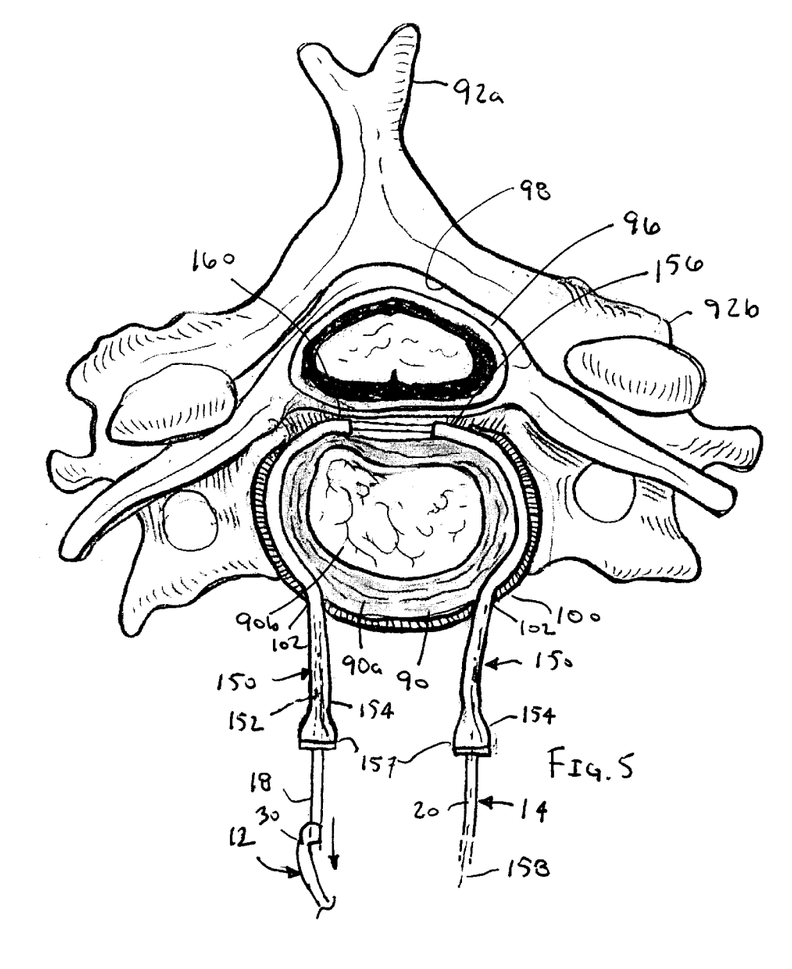
FIG. 5 is a cross-sectional view of a spinal disc of FIG. 4A, taken along line 5—5, and showing the anatomy surrounding the disc.

Turning to FIGS. 4A, 4B, and 5, another embodiment of an apparatus 110 is shown for treating a spinal disc 90. Generally, the apparatus 110 includes a grasper 12, and a band of material 14 that are substantially identical to the embodiment described above. In addition, the apparatus 110 includes a pair of guide members 150 for guiding the grasper 12 and/or the band 14 around the posterior region of the disc 90. Optionally, the apparatus 110 may also include a fork member (not shown), similar to the previous embodiment.

Each guide member 150 is a semi-rigid or substantially rigid tubular body including a slotted lumen 152 extending between its proximal and distal ends 154, 156. The proximal end 154 may be substantially straight, defining a longitudinal axis 158, and may include an enlarged proximal opening 157 (shown in FIG. 5). The distal end 156 of the guide member 150 may be curved, preferably having a radius of curvature similar to an exterior perimeter of the disc 90. The guide member 150 also has a cross-section including a height "h" (extending generally between the vertebrae adjacent the disc 90) that is greater than its width "w" (extending away from the exterior surface of the disc 90). Thus, the band 14 may be received within the lumen 152 such that the width "W" of the band 14 is substantially less than the height "h" of the guide member 150, thereby minimizing any folding or crumpling of the band 14 within the lumen 152. The distal end 156 of the guide member 150 terminates in a distal tip 160 that is disposed transversely and preferably substantially perpendicular to the axis 158.

It will be appreciated that the distal end 30 of the grasper 12 has a shape that allows the distal end 30 to be directed easily through the lumens 152 of the guide members 150. For example, the distal end 30 of the grasper 12 may have a flat ribbon shape or may have a generally round shape that is small enough to be inserted through the lumens 152.

The apparatus 110 may be used to treat a spinal disc 90 that has ruptured, become misaligned, and/or otherwise degenerated, similar to the embodiment described above. Generally, the spinal disc 90 is disposed between a first vertebra 92, best seen in FIG. 4B, and a second vertebra, which has been eliminated for clarification. The vertebrae include spinous process 92a and transverse process 92b defining a vertebral foramen 98, through which a spinal cord 96 extends. The disc 90 generally includes nucleus pulposus 90a surrounded by annulus fibrosis 90b, and is surrounded by ligament 100, which may surround the entire spinal column along its length.

Initially, the disc 90 may be accessed, preferably from an anterior approach. This may involve creating incisions 102 in the ligament 100 at locations corresponding to lateral regions of the disc 90. The distal ends 156 of the guide members 150 may be inserted through the respective incisions 102 and advanced around an exterior surface of the disc 90 until the distal tips 160 are disposed opposite one another adjacent a posterior region of the disc 90. The distal ends 156 may be sufficiently flexible to facilitate substantially atraumatic advancement of the guide members 150 around the disc 90. Once the distal ends 156 are fully inserted, the proximal ends 154 of the guide members 150 may extend proximally from the incisions 102 generally parallel to one another.

Optionally, a location of at least one of the vertebrae adjacent the disc 90 may be adjusted, for example, using traction or a fork member (not shown), before inserting the guide members 150, using a procedure similar to the embodiment described above.

With particular reference to FIG. 4A, a distal end 30 of the grasper 12 may be inserted into the lumen 152 of a first of the guide members 150 and advanced distally until the distal end 30 of the grasper 12 exits the distal end 156 of the first guide member 150 adjacent the posterior region of the disc 90. The grasper 12 may be manipulated further until the distal end 30 enters the lumen 152 at the distal end 156 of the second guide member 150, whereupon the grasper 12 may be advanced further until the distal end 30 exits the proximal end 154 of the second guide member 150.

With the distal end 30 of the grasper 12 accessible, the first end 18 of the band 14 may be connected to the distal end 30 of the grasper 12. The grasper 12 may then be pulled back through the guide members 150, thereby directing the band 14 through the lumens 152 of the guide members 150 and around the posterior region of the disc 90, as shown in FIGS. 4A and 5. Once the first end 18 of the band 14 has been pulled out of the proximal end 154 of the first guide member 150, the first end 18 of the band 14 may be released from the distal end 30 of the grasper 12.

The guide members 150 may be withdrawn from the incisions 102, leaving the band 14 in place, as shown in FIG. 4B. Because of the slotted lumens 152 of the guide members 150, the band 14 may extend completely across a height of the disc 90 and preferably at least partially covering one or both adjacent vertebrae 92. The band 14 may then be secured tightly around the disc 90, as shown in FIGS. 3A and 3B. For example, the first and second ends 18, 20 of the band 14 may be secured to one another by threads (not shown), similar to the embodiment described above. Optionally, if necessary, one or both ends 18, 20 of the band 14 may be trimmed before tightening and securing the band 14 around the disc 90.

If desired, energy may be applied to the disc 90 to enhance healing, to cause scarring, and/or to enhance sealing of fissures or other leaks in the disc 90. The energy may be applied directly to one or more regions of the disc 90 or may be applied via conductive regions of the band 14, similar to the embodiment described above.

If the band 14 is formed from bioabsorbable material, the band 14 may remain around the disc 90 until it is absorbed by the patient's body, similar to the embodiment described above. Alternatively, the band 14 may be merely biocompatible, such that the band 14 may remain within the patient's body indefinitely or until the disc 90 has sufficiently healed.

The apparatus and methods of the present invention may be performed alone or in conjunction with other procedures used to treat a spinal disc. For example, a band of material may be secured around a spinal disc after performing a procedure within an interior of a spinal disc, such as those disclosed in application Ser. No. 09/828,039, filed Apr. 6, 2001, entitled "Apparatus and Methods for Treating Spinal Discs," the disclosure of which is expressly incorporated herein by reference.

In addition, one or more guide members in accordance with the present invention may be used to access a posterior region of a spinal disc in order to perform a diagnostic and/or therapeutic procedure at the posterior region of the spinal disc. For example, an imaging device, such as an endoscope (not shown), may be inserted through the guide member to observe, monitor, or otherwise image the posterior region and/or surrounding tissue structures.

A therapeutic procedure may be performed at the posterior region of the disc, e.g., following an imaging or diagnostic procedure or concurrently with imaging (e.g., with multiple instruments, not shown, being introduced through separate guide members). A discectomy or other procedure may be performed that involves removing at least a portion of the disc from the posterior region (not shown). For example, nucleus pulposus material that has leaked from within the disc may be removed. In addition or alternatively, a prosthesis may be implanted within the disc from the posterior region. A therapeutic agent may be introduced into the posterior region or surrounding tissue to promote healing, pain relief, and the like. In addition, a band may be wrapped around the disc to stabilize the disc in a desired position relative to surrounding anatomy, as described above.

In addition, access to the posterior region of a spinal disc may be used to perform other interventions involving tissue structures adjacent to or surrounding the disc, such as the spinal cord or a spinal facet joint. Thus, instruments may be introduced between the disc and surrounding ligament, e.g., through the guide member, and directed to surrounding tissue structures in order to complete other procedures while minimizing exposure of a patient's spine.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for treating a spinal region of a patient, the method comprising:

accessing an area adjacent an anterior region of a spinal disc, the disc being disposed between adjacent vertebrae and being surrounded by a ligament;

inserting an instrument through said area and between the ligament and an exterior of the disc in order to access a posterior region of the disc; and performing a diagnostic or therapeutic procedure at a location accessed at the posterior region of the disc.

2. The method of claim 1, wherein the step of inserting an instrument comprises inserting a tubular guide member around a portion of the exterior of the disc until a distal portion of the tubular guide member is disposed adjacent the posterior region of the disc.

3. The method of claim 2, wherein the step of inserting an instrument further comprises inserting one or more instruments through the tubular guide member in order to access the posterior region.

4. The method of claim 1, wherein the step of inserting an instrument comprises inserting a pair of opposite-hand tubular guide members around opposing lateral regions of the exterior of the disc until distal ends of are disposed adjacent the posterior region.

5. The method of claim 4, wherein the step of performing a diagnostic or therapeutic procedure comprises:

directing a distal end of an elongate member through lumens of the guide members;

connecting a first end of a band to the distal end of the elongate member; and directing the distal end of the elongate member back through the lumens of the guide members to wrap the band around the posterior region of the disc.

6. The method of claim 5, wherein the band is wrapped around the disc to stabilize the disc in a desired position relative to surrounding anatomy.

7. The method of claim 1, wherein the accessing step comprises creating an incision in the ligament to access the exterior of the disc, and wherein the inserting step comprises inserting one or more instruments through the incision.

8. The method of claim 1, wherein the step of performing a diagnostic or therapeutic procedure comprises removing at least a portion of the disc.

9. The method of claim 1, wherein the step of performing a diagnostic or therapeutic procedure comprises imaging the posterior region of the disc.

10. The method of claim 1, further comprising adjusting a location of at least one of the vertebrae relative to the disc.

11. The method of claim 1, wherein the step of performing a diagnostic or therapeutic procedure comprises accessing a tissue structure adjacent the posterior region of the disc.

* * * * *